Figure 1A:
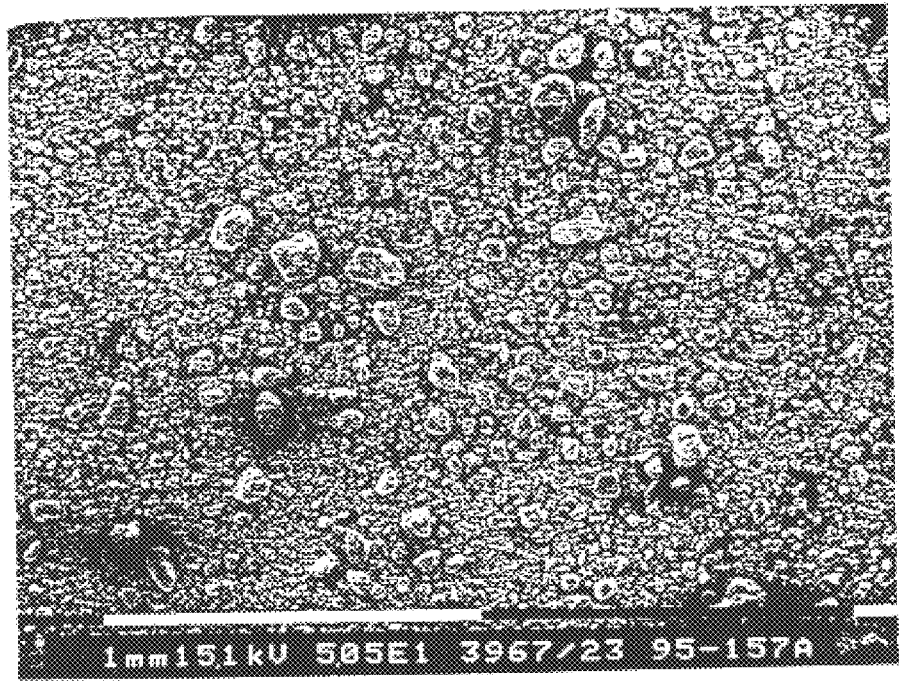

United States Patent

Tjioe

[11] Patent Number: 6,166,204
[45] Date of Patent: Dec. 26, 2000

[54] CRYSTALLINE MELAMINE

[75] Inventor: Tjay T. Tjioe, Sittard, Netherlands

[73] Assignee: DSM N.V., Heerlen, Netherlands

[21] Appl. No.: 09/266,809

[22] Filed: Mar. 12, 1999

[30] Foreign Application Priority Data

Mar. 12, 1998 [NL] Netherlands .......................... 1008571

[51] Int. Cl.$^7$ ................................................ C07D 251/60
[52] U.S. Cl. ............................................................. 544/201
[58] Field of Search ..................................... 544/201, 200

[56] References Cited

U.S. PATENT DOCUMENTS

| | | | |
|---|---|---|---|
| 4,565,867 | 1/1986 | Thomas et al. | 544/201 |
| 5,514,796 | 5/1996 | Best et al. | 544/201 |
| 5,721,363 | 2/1998 | Canzi et al. | 544/201 |
| 5,731,437 | 3/1998 | Turunen et al. | 544/201 |

FOREIGN PATENT DOCUMENTS

| | | |
|---|---|---|
| 0 747 366 | 12/1996 | European Pat. Off. . |
| 0 808 836 | 11/1997 | European Pat. Off. . |
| WO 96/23778 | 8/1996 | WIPO . |

*Primary Examiner*—Mukund J. Shah
*Assistant Examiner*—Venkataraman Balasubramanian

*Attorney, Agent, or Firm*—Pillsbury Madison & Sutro LLP

[57] ABSTRACT

Multicrystalline melamine powder having the following properties:
specific surface area: 0.7–5 $m^2/g$
level of oxygen-containing components <0.7 wt %
color APHA less than 17
melamine: >98.5 wt %
melam: <1.3 wt %

Multicrystalline melamine powder obtainable via a high-pressure process in which solid melamine is obtained by the melamine melt being transferred to a vessel where the melamine melt is cooled with an evaporating cooling medium, the melamine melt having a temperature between the melting point of melamine and 450° C. being treated with 0.1–15 mol of ammonia per mole of melamine and then being sprayed via spraying means and cooled with an evaporating cooling medium within a vessel in an ammonia environment at an ammonia pressure of 0.1–25 MPa, the melamine melt being converted into melamine powder having a temperature between 200° C. and the solidification point of melamine, the melamine powder then being cooled to a temperature below 50° C., the powder being set in motion mechanically over at least part of the cooling range and being cooled directly or indirectly, and the ammonia pressure being released at a temperature below 270° C.

28 Claims, 2 Drawing Sheets

CRYSTALLINE MELAMINE

The invention relates to crystalline melamine, more in particular to multicrystalline melamine powder.

Melamine is prepared in various ways on an industrial scale. Methods exist which ultimately involve the crystallization of melamine from an aqueous solution, a process exists in which melamine is obtained directly from a gaseous phase, and a method exists which involves the synthesis of melamine at high pressure (7–25 MPa), and where the melamine melt obtained thereby is sprayed in an ammonia atmosphere and is cooled, said crystalline powder lending itself to being used as such without further purification steps.

Crystalline melamine obtained according to the first method consists of a very pure melamine, but the crystals are relatively large, so that the rate of dissolution in a solvent such as, for example, water or a water/formaldehyde mixture is not optimal. The melamine thus obtained is usually ground to afford more suitable particles. Smaller particles have a higher rate of dissolution but a lower bulk density and poorer flow characteristics. As a result, an optimal product in terms of combination of rate of dissolution, bulk density and flow characteristics is not obtained. Melamine obtained directly from the gas phase is very fine and consequently also has relatively poor flow characteristics. Crystalline melamine obtained according to the method which involves spraying a melamine melt is a multicrystalline melamine powder having good dissolution and reactivity characteristics in combination with what for melamine are reasonable flow characteristics. This melamine powder in practice, however, is found to contain a high concentration of impurities (in particular melam). To reduce the melam concentration, a method has been proposed of spraying the melamine at a relatively high pressure, such as described in EP-A-747366.

In particular, EP-A-747366 describes how urea is pyrolysed in a reactor at a pressure of from 10.34 to 24.13 MPa and a temperature of from 354 to 454° C. to produce a reactor product. The reactor product obtained contains liquid melamine, $CO_2$ and $NH_3$ and is transferred under pressure as a mixed stream to a separator. In this separator, which is kept at virtually the same pressure and temperature as the said reactor, the said reactor product is separated into a gaseous stream and a liquid stream. The gaseous stream contains $CO_2$ and $NH_3$, waste gases and also melamine vapour. The liquid stream mainly comprises liquid melamine. The gaseous product is transferred to a scrubber unit, while the liquid melamine is transferred to a product-cooling unit. In the scrubber unit, the said $CO_2$ and $NH_3$ waste gases, which contain melamine vapour, are scrubbed with molten urea, at virtually the same pressure and temperature as the pressure and temperature of the reactor, to preheat the urea and to cool the said waste gases to a temperature of 177–232° C. and to remove the melamine present from the waste gases. Then the preheated molten urea, which contains the said melamine, is fed to the reactor. In the product-cooling unit, the liquid melamine is cooled with a liquid cooling medium, which forms a gas at the temperature of the liquid melamine in the product cooler, to produce a solid melamine product without scrubbing or further purification. EP-A-747366 preferentially uses liquid ammonia as the liquid cooling medium, the pressure in the product-cooling unit being above 41.4 bar. The purity of the melamine end product, according to EP-A-747366, is above 99 wt %. Examples of other publications directed at the lowering of the melam concentration include WO-A-96/20182, WO-A-96/20183 and WO-A-96/23778. None of these publications, however, address other characteristics of the melamine such as colour and specific surface area. The methods described are often found to yield a product exhibiting a yellow colour. Particularly in the case of melamine-formaldehyde resins used in laminates and/or coatings this is unacceptable. On a commercial scale this is a drawback, since too much product is made that does not meet the product specifications.

The object of the present invention is to obtain improved crystalline melamine powder, where melamine is to be obtainable with a high degree of purity as a dry powder direct from a melamine melt. More in particular the object of the present invention is to obtain crystalline melamine powder with a high dissolution rate in water, acceptable flow characteristics, a high purity and a good colour.

The invention relates to multicrystalline melamine powder having the following properties:

colour APHA less than 17 a purity of greater than 98.5 wt % of melamine less than 1.3 wt % of melam level of oxygen-containing components below 0.7 wt % a specific surface area of between 0.7 and 5 $m^2/g$

This product differs from melamine powder obtained from gaseous melamine or from melamine crystallized from water in terms of its larger specific surface area. This product further differs from melamine powder obtained from gaseous melamine in terms of the larger particles, as a result of which the melamine powder according to the invention has better flow characteristics and higher bulk density. Moreover, the product according to the invention differs from melamine crystallized from water in terms of a higher rate of dissolution (given an identical particle size distribution) due to the larger specific surface area.

One customary method for determining the colour of melamine is by so-called APHA colorimetry. This involves the preparation of a melamine-formaldehyde resin with an F/M ratio of 3, a formaldehyde solution being used which contains 35 wt % of formaldehyde, between 7.5 and 11.2 wt % of methanol and 0.028 wt % of acid (as formic acid). The theoretical solids content of the solution is 56 wt %. 25 g of melamine are dissolved in 51 g of the above solution by the mixture being heated rapidly to 85° C. After about 3 minutes, all the melamine has dissolved. This solution is admixed with 2 ml of a 2.0 mol/l sodium carbonate solution, the resulting mixture being stirred for 1–2 minutes. Then the mixture is rapidly cooled to 40° C. The colour is determined by means of a Hitachi U100 spectrophotometer with a 4 cm glass cuvette, by absorbance measurements being carried out on the abovementioned solution at a wavelength of 380 nm and 640 nm, using deionized water as a blank in the reference cuvette. The APHA colour is calculated by means of the following formula:

$$APHA = f*(E380 - E640)$$

where

E380=absorbance at 380 nm;

E640=absorbance at 640 nm;

f=calibration factor.

The calibration factor f is determined on the basis of absorbance measurements at 380 nm on calibration solutions prepared from cobalt chloride and potassium hexachloroplatinate. A 500 APHA calibration solution contains 1.245 g of potassium hexachloroplatinate(IV), 1.000 g of cobalt(II) chloride and 100 ml of 12 M hydrochloric acid solution per liter of calibration solution. With the aid of this calibration solution dilutions are prepared for calibrations at 10 and 20

APHA. The calibration factor f is calculated by means of the following formula:

$$f=APHA\text{(calibration solution)}/E380$$

where APHA (calibration solution)=APHA value of the calibration solution and E380=absorbance at 380 nm.

The colour of the melamine obtained with the method according to the invention is less than 17 APHA, preferably less than 15 APHA and in particular less than 12 APHA.

Another yardstick for the colour is the yellowness of the product. The yellowness of the product can be measured in accordance with the Hunterlab-C.I.E. method. According to this method, 60 g of melamine powder are introduced into a cuvette of a Hunterlab ColorQUEST® spectrophotometer. The measurement is carried out in accordance with the Hunterlab method C.I.E., values being determined for L', a' and b'. The value of b' in the Hunterlab-C.I.E. method is a yardstick for the blue-yellow shift. In the case of a positive value the product is yellow and in the case of a negative value blue. An increase in the positive value means a yellower product.

The colour of the melamine powder preferably has a value for b' of less than 1, particularly preferably less than about 0.8, because resins produced from this melamine are entirely water-white.

A customary method for determining the specific surface area is with the aid of gas adsorption according to the BET method. For a description of the BET method see S. Brunauer, P. H. Emmett, E. Teller; J. Am. Chem. Soc.; 60 (1938) 309.

The specific surface area is preferably between 0.9 and 3 m$^2$/g.

Examples of other characteristic properties of the product of the present invention are:
pore volume of the powder: 0.35–0.65 cm$^3$/g
urea content: <0.3 wt %
ureidomelamine content: <0.3 wt %
ammeline content: <0.1 wt %
ammelide content: <0.01 wt %
cyanuric acid content: <0.01 wt %
guanidine content: <0.04 wt %
melem content: <0.1 wt %

The level of oxygen-containing components is preferably below 0.4 wt %.

The concentration of melam in the melamine powder is preferably less than 1.0 wt %, more particularly less than 0.5 wt %.

The purity of the melamine is preferably greater than 99 wt %, more particularly between 99.5 and 99.8 wt %, because this comes close to the purity of melamine crystallized from water.

Figure 1B:
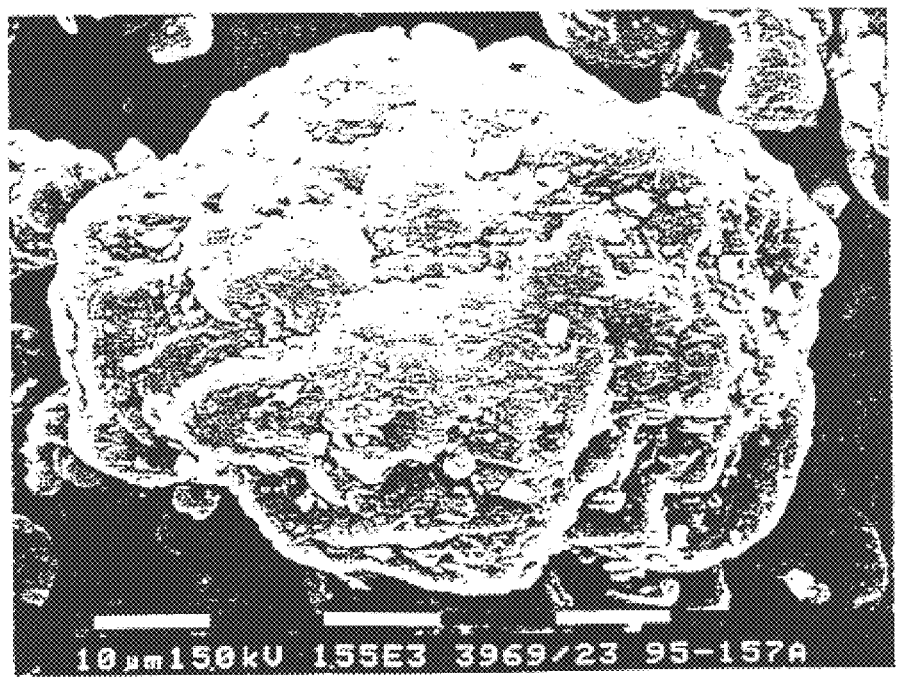
Figure 2A:
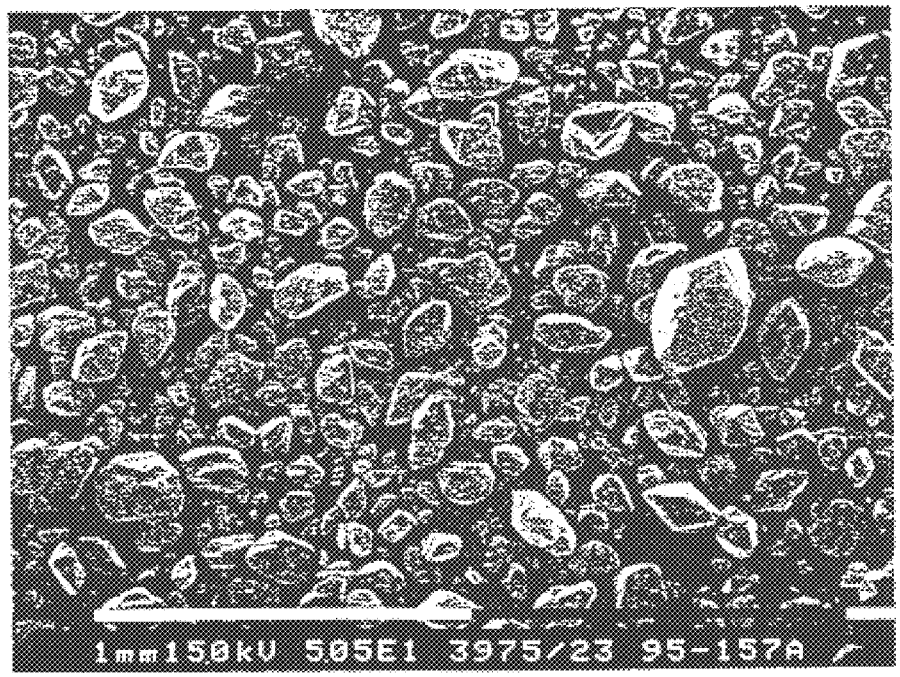
Figure 2B:
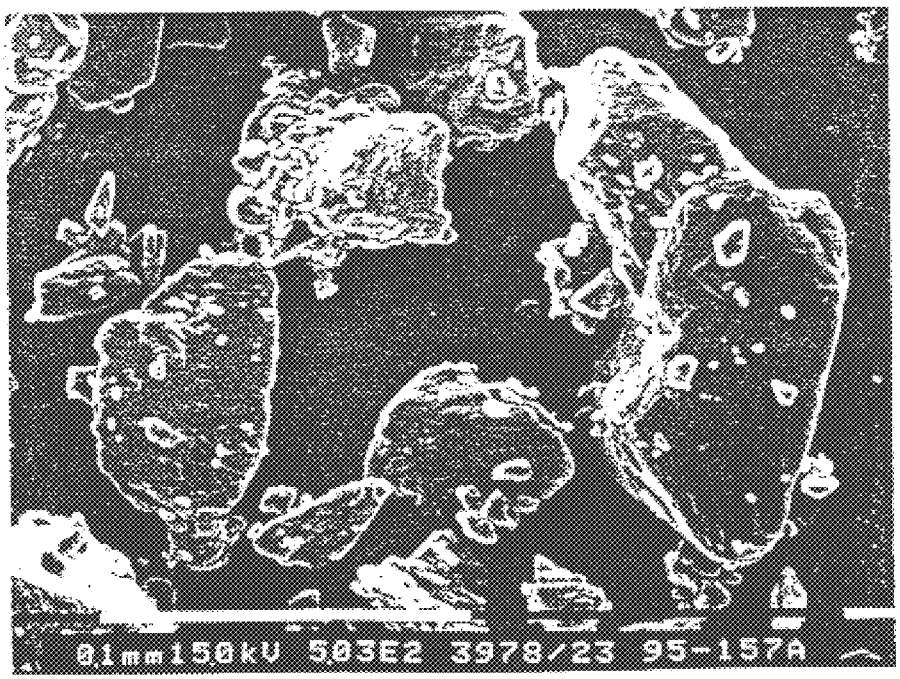

Said melamine powder according to the invention consists of multicrystalline particles. This means that the larger particles (>20 µm) are composed of a multiplicity of crystals. On a scanning electron micrograph these particles can be clearly distinguished from melamine crystallized from water. The particles according to the invention have a cauliflower-like structure. The melamine crystallized from water, in contrast, contains a substantial amount of crystals having a crystal size greater than 50 µm. On the SEM pictures the crystallographic crystal faces (large relatively flat areas) in the case of melamine crystallized from water are clearly discernible. These structures can be seen on FIGS. 1 and 2; FIG. 1 comprises SEM pictures (FIG. 1A: 50×and FIG. 1B: 1500×) of particles having a so-called cauliflower structure, whereas FIG. 2 comprises SEM pictures of melamine crystallized from water (FIG. 2A: 50× and FIG. 2B: 500×). The photographs of the products were produced using a Philips SEM 515 at an accelerating voltage of 15 kV.

The applicant has now also found that melamine can be produced with continuously high purity by the melamine melt which comes from the melamine reactor and has a temperature between the melting point of melamine and 450° C. first being treated with gaseous ammonia (0.1–15 mol of ammonia per mole of melamine) and then being sprayed via spraying means and cooled by means of an evaporating cooling medium within a vessel in an ammonia environment at an ammonia pressure of 0.1–25 MPa, the melamine melt being converted into melamine powder having a temperature below 50° C., other cooling methods also being used if required. If required, the powder can be further cooled in the same vessel or in another vessel by the powder being set in motion mechanically and being cooled directly or indirectly.

Melamine powder has poor flow and fluidization characteristics and a low temperature equalization coefficient (poor thermal conductivity). Standard cooling methods such as a fluidized bed or a packed moving bed can therefore not readily be implemented on a commercial scale. The applicant has found, however, that the colour of the melamine powder, in particular, is adversely affected if the melamine remains at a high temperature for too long. Effective control of the dwell time at high temperature has therefore proved critical. It is therefore important to be able to cool the melamine powder effectively.

Surprisingly, it proved possible to cool melamine powder rapidly, despite the poor flow characteristics, by setting it in motion mechanically and at the same time cooling it directly or indirectly. Indirect cooling means that the mechanically agitated bed of melamine powder is brought into contact with a cooling surface. Direct cooling means that the mechanically fluidized bed is brought into contact with a cooling medium, for example ammonia or an air stream. A combination of direct and indirect cooling is obviously also possible.

In one embodiment, the powder obtained by spraying remains in contact with ammonia at a pressure of 0.1–25 MPa and at a temperature above 200° C. over a period of preferably 1 min–5 hours, particularly preferably over a period of 5 min–2 hours, since this results in a decrease in the percentage of impurities.

During this contact time, the product can remain at virtually the same temperature or be cooled down in such a way that the product over the desired period has a temperature above 200° C., preferably above 240° C. and in particular above 270° C. At higher temperatures a higher ammonia pressure should be chosen. At 240° C., the ammonia pressure should be greater than 0.2 MPa, and at 270° C., the ammonia pressure should be greater than 0.5 MPa.

Preferably, the dwell time at a temperature above 200° C. is such that the discoloration is less than the discoloration corresponding to a b' of about 1. At lower temperature a longer dwell time is permitted before yellowing exceeds the specification. At higher temperature a shorter dwell time is permitted.

The advantage of the method according to the present invention is that a powdered melamine is obtained with a purity which is continuously above 98.5 wt % or preferably above 99 wt %, which is sufficient for the melamine thus obtained to be used in virtually any melamine application. At the same time it is possible to obtain melamine powder having very good colour characteristics.

The preparation of melamine preferably starts from urea as the raw material in the form of a melt. NH$_3$ and CO$_2$ are by-products during the preparation of melamine, which proceeds according to the following reaction equation:

$$6\ CO(NH_2)_2 \rightarrow C_3N_6H_6 + 6\ NH_3 + 3\ CO_2$$

The preparation can be carried out at high pressure, preferably between 5 and 25 MPa, without the presence of a catalyst. The reaction temperature varies between 325 and 450° C. and is preferably between 350 and 425° C. The by-products $NH_3$ and $CO_2$ are usually recycled to an adjoining urea factory.

The abovementioned objective of the invention is achieved by employing an apparatus suitable for the preparation of melamine from urea. An apparatus suitable for the present invention may comprise a scrubber unit, a reactor in conjunction with a gas/liquid separator or with a separate gas/liquid separator, optionally a post-reactor, a first cooling vessel and optionally a second cooling vessel.

In one embodiment of the method, melamine is prepared from urea in an apparatus comprising a scrubber unit, a melamine reactor optionally in conjunction with a gas/liquid separator or a separate gas/liquid separator, a first cooling vessel and a second cooling vessel. This involves urea melt from a urea factory being fed to a scrubber unit at a pressure of from 5 to 25 MPa, preferably from 8 to 20 MPa, and at a temperature above the melting point of urea. This scrubber unit may be provided with a cooling jacket in order to ensure additional cooling within the scrubber. The scrubber unit may also be provided with internal cooling bodies. In the scrubber unit the liquid urea comes into contact with the reaction gases from the melamine reactor or from a separate gas/liquid separator downstream of the reactor. The reaction gases mainly consist of $CO_2$ and $NH_3$ and also comprise some melamine vapour. The molten urea scrubs the melamine vapour from the waste gas and carries this melamine along back to the reactor. In the scrubbing process, the waste gases are cooled from the temperature of the reactor, i.e. from 350 to 425° C., to from 170 to 270° C., the urea being heated to from 170 to 270° C. The waste gases are removed from the top of the scrubber unit and, for example, recycled to a urea factory, where they are used as a raw material for the urea production.

The preheated urea is drawn off from the scrubber unit, together with the melamine scrubbed out, and supplied, for example via a high-pressure pump, to the reactor which has a pressure of from 5 to 25 MPa and preferably of from 8 to 20 MPa. Alternatively, the transfer of the urea melt to the melamine reactor may be effected by gravity, by the scrubber unit being positioned above the reactor.

In the reactor, the molten urea is heated to a temperature of from 325 to 450° C., preferably of from approximately 350 to 425° C., at a pressure as reported above, under which conditions the urea is converted into melamine, $CO_2$ and $NH_3$. A certain amount of ammonia can be metered into the reactor, for example in the form of a liquid or hot vapour. The ammonia supplied may serve, for example, to prevent the formation of condensation products of melamine such as melam, melem and melon, or to promote mixing in the reactor. The amount of ammonia supplied to the reactor is from 0 to 10 mol per mole of urea, from 0 to 5 mol of ammonia preferably being used and in particular from 0 to 2 mol of ammonia per mole of urea.

The $CO_2$ and $NH_3$ produced in the reaction as well as the additionally supplied ammonia collect in the separation section, for example in the top of the reactor, although a separate gas/liquid separator positioned downstream of the reactor is also possible, and are separated in the gaseous state from the liquid melamine. If a separate gas/liquid separator downstream of the reactor is employed, it may be advantageous for ammonia to be metered into this separator. The amount of ammonia in this case is 0.1–15 mol of ammonia per mole of melamine, preferably 0.3–10 mol. This has the advantage that the carbon dioxide is rapidly separated off, thus inhibiting the formation of oxygen-containing by-products. At a higher pressure in the reactor, a larger amount of ammonia should be used than at a lower reactor pressure.

The gas mixture formed downstream of the gas/liquid separation is passed to the scrubber unit in order to remove melamine vapour and preheat the urea melt.

The liquid melamine having a temperature between the melting point of melamine and 450° C. is drawn off from the reactor or from the gas/liquid separator downstream of the reactor and, prior to spraying, may be cooled to a temperature above the melting point of melamine.

Preferably, the liquid melamine having a temperature above 390° C., more in particular above 400° C. is cooled by at least 5° C. and in particular at least 15° C. More in particular, the melt is cooled to a temperature which is 5–20° C. above the solidification point of melamine. Cooling can take place in the gas/liquid separator or in a separate apparatus downstream of the gas/liquid separator. Cooling can take place by injection of a cooling medium, for example ammonia gas having a temperature below the temperature of the melamine melt, or by means of a heat exchanger.

Furthermore, ammonia can be introduced into the liquid melamine in such a way that a gas/liquid mixture is sprayed in the spraying means.

The pressure of introduced ammonia in this case is above the pressure of the melamine melt and preferably between 10 and 45 MPa, and in particular between 15 and 30 MPa.

The residence time of the liquid melamine between the reactor and the spraying means is preferably greater than 10 minutes, in particular greater than 30 minutes. The residence time will usually be below 7 hours, preferably less than 5 hours.

The melamine melt, possibly together with ammonia gas, is transferred to a first vessel in which the liquid melamine melt is sprayed via spraying means in an ammonia environment and cooled with a gaseous or evaporating medium at an ammonia pressure of 0.1–25 MPa, preferably 1–11 MPa, a powder being formed which, after optional further cooling, has a temperature below 50° C.

The spraying means is an apparatus by which the melamine melt is converted into droplets or powder, by causing the melt to flow at high speed into the cooling vessel. The spraying means may be a nozzle or valve. The outflow velocity of the liquid from the spraying means as a rule is greater than 20 m/s, preferably greater than 50 m/s. With greater outflow velocities, for a given pressure and temperature in the cooling vessel, a higher purity of the product is obtained. The outflow velocity of the liquid (in m/s) is defined as the mass flow through the valve or nozzle (in kg/s) divided by the smallest effective area of flow in the valve or nozzle (in $m^2$) and divided by 1000 $kg/m^3$, this being the approximate density of the liquid. The melamine droplets from the spraying means are cooled by a gaseous or evaporating cooling medium to give a powder. This cooling medium may be cold ammonia gas or liquid ammonia, for example. The (liquid) ammonia may (in part) already be present in the melamine melt and/or be sprayed into the first vessel.

In one embodiment of the invention, the product having a pressure greater than 15 MPa is sprayed via a spraying means and cooled very rapidly in accordance with the above method, the outflow velocity being greater than 100 m/s, to a temperature below 240° C. and preferably below 150° C., followed by rapid further cooling to a temperature below 50° C. The further cooling can take place in a cooling apparatus in which the powder is set in motion mechanically, or in an apparatus in which the powder is conveyed pneumatically or during storage by free convection/heat conduction or a combination of the above methods. Preferably the product, after the ammonia pressure has been released, should be cooled within one hour to a temperature below 150° C.

In another embodiment, the melamine powder, after spraying, is cooled to a temperature below 50° C., the powder being set in motion mechanically over at least part of the cooling range and being cooled directly or indirectly, and the ammonia pressure being released at a temperature below 270° C.

In one embodiment, the powder obtained by spraying preferably remains in contact with ammonia over a period of 1 min–5 hours, particularly preferably over a period of 5 min–2 hours at a pressure of 0.5–25 MPa, preferably 1–11 MPa and at a temperature above 200° C. During this contact time, the powder can remain at virtually the same temperature or be cooled down.

The ammonia pressure is preferably released when the melamine powder has a temperature below 270° C., more in particular below 200° C.

If the melamine is sprayed and cooled to a temperature above 270° C., it is preferable for the means for setting the melamine powder in motion mechanically and cooling it to be used at an ammonia pressure of 0.5–25 MPa. However, if the melamine melt is sprayed and cooled to a temperature below 270° C., preferably below 240° C. and in particular to a temperature below 200° C., these means can be used at a lower pressure (0.05–0.2 MPa), which is advantageous because of lower investment costs.

The powder obtained by spraying can be processed batchwise or continuously. In the case of batchwise processing use will generally be made of at least two vessels in which the liquid melamine can be sprayed, the vessels being used alternately. As soon as a first vessel contains the desired amount of melamine powder, the spraying device can be shut off, and filling of the next vessel can be started. During that time, the contents of the first vessel can be treated further. In the case of a continuous process, the liquid melamine will generally be sprayed within a first vessel, after which this vessel is emptied into a second vessel, in which the cooling step can then take place. Obviously, a hybrid of the two methods can be employed.

In one embodiment of the invention, the melamine melt is preferably cooled during spraying to a temperature between 160° C. and 10° C. below the solidification point. The melamine powder thus obtained is preferably cooled by at least 35° C., more preferably by at least 60° C., by the powder being set in motion mechanically and being cooled directly or indirectly.

Cooling is effected with the aid of an apparatus provided with means for moving powder mechanically and provided with means for cooling powder directly or indirectly.

Examples of means for moving powder mechanically include a screw and rotating drum, a rotating bowl, rotating discs, rotating segment discs, rotating pipes and the like.

The powder can be cooled indirectly by the surface of the fixed and/or moving parts of the apparatus being cooled, for example with cooling fluid such as water or oil.

The effective heat transfer coefficient of a suitable cooling apparatus involving indirect cooling is preferably between 10 and 300 W/m²K, based on the cooling area of the apparatus.

Preference is given to the use of a cooling apparatus which comprises means having a cooling area of 50–5000 m².

The powder can be cooled directly by a gaseous or evaporating cooling medium being injected into the vessel, preferably ammonia gas or ammonia liquid.

Obviously it is also possible for a combination of direct and indirect cooling to be used.

This cooling apparatus is highly suitable both for cooling melamine powder at high pressure (0.5–25 MPa) and at low pressure (0.05–0.2 MPa) to a temperature of about 50–70° C.

Preferably, ammonia gas is completely removed (to an amount below 1000 ppm, preferably less than 300 ppm and in particular less than 100 ppm) by air being blown through.

The invention will be explained in more detail with reference to the following example.

EXAMPLE

Melamine melt having a temperature of 360° C. and a pressure of 18 MPa is treated with 0.8 kg of ammonia per kg of melamine. The melamine is then introduced, via a spraying device, into a high-pressure vessel at an outflow velocity greater than 100 m/s and very rapidly cooled with liquid ammonia which is likewise sprayed into the vessel. The temperature in the vessel is 233° C. The high-pressure vessel is designed as a rotating drum provided with a wall which can be cooled, and provided with a gas inlet. The ammonia pressure in the vessel varies between 5.4 and 8.2 MPa. After 1 minute the product is cooled to ambient temperature. The cooling step to 200° C. took 5 minutes. When the melamine powder has a temperature of about 180° C., all the $NH_3$ is released and air is metered into the vessel. The end product has the following properties:

specific surface area: 1.2 m²/g
level of oxygen-containing components: 0.12 wt %
colour (APHA): 10
99.3 wt % of melamine
0.4 wt % of melam
<0.1 wt % of melem
concentration of ammonia 50 ppm Comparative Example Melamine melt of 400° C., held in a vessel under an ammonia pressure of 13.6 MPa, is rapidly cooled to ambient temperature by the vessel being brought into contact with a mixture of ice and water. The end product contains 1.4 wt % of melam and 0.4 wt % of melem. The specific surface area is 0.3 m²/g.

What is claimed is:

1. Multicrystalline melamine powder having the following properties:
    specific surface area: 0.7–5 m²/g
    level of oxygen-containing components <0.7 wt %
    colour APHA less than 17
    melamine: >98.5 wt %
    melam: <1.3 wt %.

2. Multicrystalline melamine powder according to claim 1, characterized in that the specific surface area is between 0.9 and 3 m²/g.

3. Multicrystalline melamine powder according to claim 1, characterized in that the colour is lower than 15 APHA.

4. Multicrystalline melamine powder according to claim 1, characterized in that the concentration of the melam is less than 1.0 wt %.

5. Multicrystalline melamine powder according to claim 1, characterized in that the purity of the melamine powder is greater than 99 wt %.

6. Multicrystalline melamine powder according to claim 5, characterized in that the purity of the melamine powder is at least 99.5 wt %.

7. Multicrystalline melamine powder according to claim 1, characterized in that the level of oxygen-containing components is below 0.4 wt %.

8. Multicrystalline melamine powder according to claim 1, characterized in that the yellowing of the melamine powder (b') is less than 1.

9. Multicrystalline melamine powder according to claim 8, characterized in that the yellowing of the melamine powder (b') is less than 0.8.

10. Multicrystalline melamine powder obtainable via a high-pressure process in which solid melamine is obtained by the melamine melt being transferred to a vessel where the melamine melt is cooled with an evaporating cooling medium, characterized in that the melamine melt having a temperature between the melting point of melamine and 450° C. is treated with 0.1–15 mole of ammonia per mole of melamine and is then sprayed via spraying means and cooled with an evaporating cooling medium within a vessel in an ammonia environment at an ammonia pressure of 0.1–25 MPa, the melamine melt being converted into melamine powder having an initial temperature between 200° C. and the solidification point of melamine, the melamine powder then being cooled to a final temperature below 50° C., the initial temperature and final temperature defining a cooling range, the powder being set in motion mechanically over at least part of the cooling range and being cooled directly or indirectly, and the ammonia pressure being released at a temperature below 270° C.

11. Multicrystalline melamine powder obtainable according to claim 10, characterized in that the powder remains in contact with ammonia at a pressure of 0.1–25 MPa over a period of between 1 minute and 5 hours, wherein during said period the temperature of the melamine powder remains virtually the same or decreases.

12. Multicrystalline melamine powder obtainable according to claim 10, characterized in that the melamine melt is sprayed via spraying means within a vessel in an ammonia environment at a pressure of 0.5–11 MPa.

13. Multicrystalline melamine powder obtainable according to claim 10, characterized in that the melamine melt is converted into melamine powder having a temperature between 240° C. and the solidification point of melamine.

14. Multicrystalline melamine powder obtainable according to claim 13, characterized in that the melamine melt is converted into melamine powder having a temperature between 270° C. and the solidification point of melamine.

15. Multicrystalline melamine powder obtainable according to claim 10, characterized in that the powder remains in contact with ammonia over a period of between 5 minutes and 2 hours.

16. Multicrystalline melamine powder obtainable according to claim 10, characterized in that the powder remains in contact with ammonia at a pressure of 0.5–11 MPa.

17. Multicrystalline melamine powder obtainable according to claim 10, characterized in that the powder obtained by spraying is further cooled by means of an apparatus provided with means for moving the melamine powder mechanically and provided with means for cooling powder directly or indirectly.

18. Multicrystalline melamine powder obtainable according to claim 17, characterized in that the means for moving the melamine powder mechanically comprise a rotating screw, drum, bowl, discs, disc segments or pipes.

19. Multicrystalline melamine powder obtainable according to claim 17, characterized in that the apparatus has an effective heat transfer coefficient of 10–300 W/m$^2$K, based on the cooling area.

20. Multicrystalline melamine powder obtainable according to claim 17, characterized in that the apparatus has a cooling area of 50–5000 m$^2$.

21. Multicrystalline melamine powder obtainable according to claim 10, the ammonia pressure being released at a temperature below 250° C.

22. Multicrystalline melamine powder obtainable according to claim 21, the ammonia pressure being released at a temperature below 200° C.

23. Multicrystalline melamine powder obtainable according to any one of claims 10 or 18, wherein the melamine powder is set in motion mechanically and is cooled directly or indirectly over at least part of the cooling range, the part of the cooling range being at least 35° C.

24. Multicrystalline melamine powder obtainable according to claim 23, wherein the part of the cooling range is at least 60° C.

25. Multicrystalline melamine powder obtainable according to any one of claims 10 or 18, the means for setting the melamine powder in motion mechanically and cooling it being used at a pressure between 0.5 and 25 MPa.

26. Multicrystalline melamine powder obtainable according to claim 18, the means for setting the melamine powder in motion mechanically and cooling it being used at a pressure from 0.05 to 0.2 MPa.

27. Multicrystalline melamine powder, characterized in that the melamine melt having a temperature between the melting point of melamine and 450° C. is treated with 0.1–15 mol of ammonia per mole of melamine at an ammonia pressure greater than 15 MPa and is then sprayed at an outflow velocity greater than 100 m/s and is cooled with an evaporating cooling medium to a temperature below 240° C.

28. Multicrystalline melamine powder according to claim 27, characterized in that the melamine melt is cooled with an evaporating cooling medium to a temperature below 150° C.

* * * * *